United States Patent [19]

Bachet et al.

[11] 4,368,422
[45] Jan. 11, 1983

[54] NON-DESTRUCTIVE TESTING METHOD AND APPARATUS FOR SPOT WELDS

[75] Inventors: Bernard Bachet, Marsannay la Cote; Claude Doucelance, Talant, both of France

[73] Assignee: Commissariat a l'Energie Atomique, Paris, France

[21] Appl. No.: 212,149

[22] Filed: Dec. 2, 1980

[30] Foreign Application Priority Data

Dec. 14, 1979 [FR] France ............................... 79 30700

[51] Int. Cl.³ ............................................ G01R 27/14
[52] U.S. Cl. .................................... 324/64; 324/65 P
[58] Field of Search ............................... 324/64, 65 P; 219/78.01, 86.1

[56] References Cited

U.S. PATENT DOCUMENTS

| | | | |
|---|---|---|---|
| 2,142,619 | 1/1939 | Sciaky | 324/64 |
| 3,192,474 | 6/1965 | Cherry | 324/64 X |
| 3,303,418 | 2/1967 | Rose | 324/64 |
| 3,611,125 | 10/1971 | Press et al. | 324/64 |
| 3,735,253 | 5/1973 | Seger | 324/64 |
| 3,916,304 | 10/1975 | Roemer et al. | 324/64 |

FOREIGN PATENT DOCUMENTS 1498864 9/1967 France .
2400706 3/1979 France .
1282812 7/1972 United Kingdom .

OTHER PUBLICATIONS

Pivinchny et al., Four-Point Method Tests Solder Joints, Electronics, Apr. 3, 1975, pp. 106, 107.

*Primary Examiner*—Stanley T. Krawczewicz
*Attorney, Agent, or Firm*—Kerkam, Stowell, Kondracki & Clarke

[57] ABSTRACT

The present invention relates to method and to an apparatus for the non-destructive testing of spot welds and the determination of the diameter of a spot weld. The testing method comprises subjecting the welds (2) to a mechanical test using a pneumatic hammer and during the test the so-called "stuck" welds are destroyed. The remaining welds then undergo a punctiform inspection using a rheometric method. This method consists of creating a potential difference between the supply electrodes (10), of which there are even numbers in contact with the weld (2). Measuring electrodes (8) located in the vicinity of the supply electrodes make it possible to obtain a resulting quantity of the different voltages measured. After calibrating the resulting value of the voltages makes it possible to deduce therefrom the diameter of the weld and consequently its efficiency.

Application to the determination of the diameter of a spot weld.

8 Claims, 6 Drawing Figures

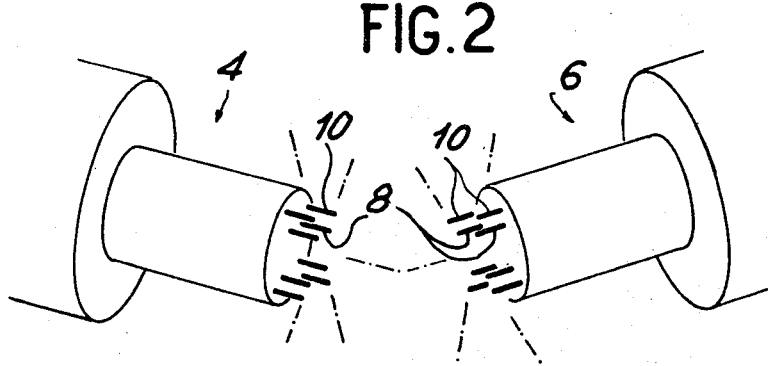
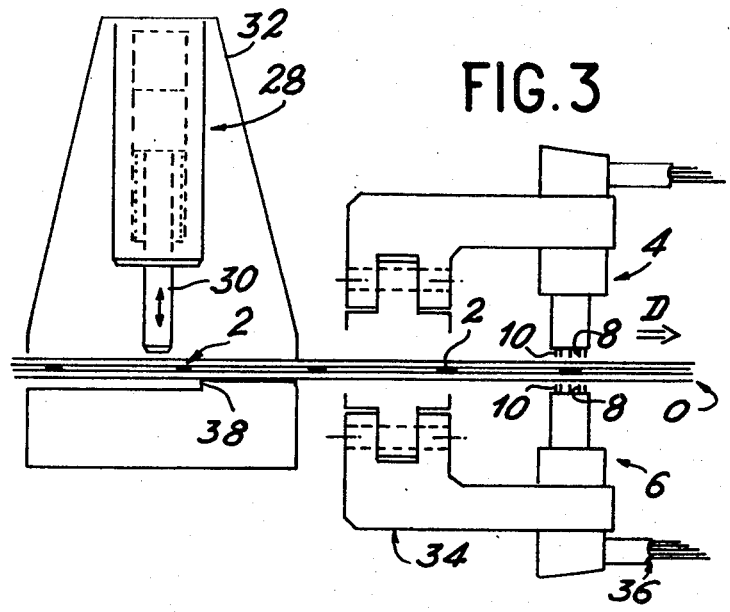
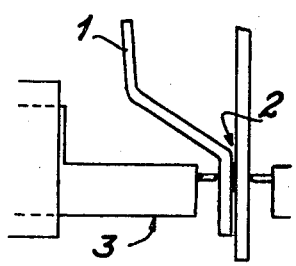
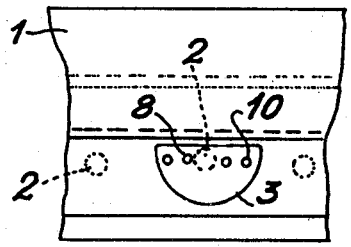

NON-DESTRUCTIVE TESTING METHOD AND APPARATUS FOR SPOT WELDS

BACKGROUND OF THE INVENTION

The present invention relates to a method and to an apparatus for the non-destructive testing of spot welds.

The invention more particularly relates to a method making it possible to measure the diameter of welds and deduce therefrom the effectiveness of these welds.

Several non-destructive testing methods have been proposed for industrially controlling spot welds. These methods include the Fokker method and signature analysis by mechanical impedance.

The Fokker method which is used for controlling the cohesion of an adhesive joint between metal plates cannot be used for the inspection of spot welds. The reason is that the surface state of the welds is not identical between individual welds. As a result there are coupling variations between the structure of the welds and the piezoelectric transducer making it possible to carry out this method. These variations mask the variations due to the quality of the welds.

The second method, which is based on signature analysis by mechanical impedance has given better results than the aforementioned method. This method, which is very difficult to perform, uses a system of measurements and apparatuses for plotting a mechanical impedence diagram permits the overall testing of the soundness of all the welds in a metal member. However, it does not permit the individual control of welds or the determination of the diameter of each weld.

BRIEF SUMMARY OF THE INVENTION

The object of the invention is to obviate these advantages and to make it possible to measure the diameter of a weld and consequently deduce therefrom its efficiency. In addition, the method for the non-destructive testing of spot welds is easy to perform and is independent of the surface state of the weld.

The invention therefore relates to a process and to an apparatus for the non-destructive testing of spot welds.

The process according to the invention is characterized in that the welds firstly undergo a mechanical test making it possible to inspect the welds during which the so-called "stuck" welds are destroyed and the others remain intact, followed by a punctiform inspection of each point of the remaining weld using a rheometric method.

The mechanical test according to the invention which makes it possible to destroy the so-called "stuck" welds comprises creating a certain number of impacts or shocks around the welded area or on the weld being studied. This is performed for a very short time using a percussive tool. This tool is fixed to a column and is connected to a solenoid valve, so that the impact point is reproducible.

According to an essential feature of the invention the punctiform inspection of each weld point is carried out by a rheometric method consisting of circulating between a single or more pairs of electrodes in contact with the welded area under investigation an electrical current. A potential difference is then measured at the terminals of one or more other pairs of electrodes. This potential difference assumes a clearly defined value for a given current in the case of a sound weld, whereas the potential difference is subject to variations in the case of any disturbance or special feature within the weld.

Moreover, in the case of a sound weld the potential difference makes it possible to deduce in a simple manner the diameter of the weld and therefore its effectiveness.

According to another feature of the invention the apparatus for performing the non-destructive testing method for spot welds comprises a detection system formed by two identical measuring heads, each constituted by n pairs of measuring electrodes and n pairs of supply electrodes, each pair of said supply electrodes being associated with a pair of measuring electrodes, the two measuring heads being arranged symmetrically on the welded area under investigation and are connected to a stabilized direct current supply, to a measuring system and to a visual display device.

Moreover, each pair of measuring electrodes is aligned with the pair of supply electrodes associated therewith and is positioned symmetrically with respect to the centre of the weld in such a way that the measuring electrodes of one and the same pair are spaced by at the most 11 mm and each associated supply electrode is spaced by at the most 2 mm from each measuring electrode. The measuring electrodes of one and the same measuring head are electrically interconnected so as to measure the resulting quantity of the measured potential differences, whilst the supply electrodes of one and the same measuring head are interconnected via a resistor making it possible to obtain a constant current in each supply electrode.

This apparatus has a certain number of advantages and in particular the intensity of the current used for supplying the electrodes is relatively low, so that the installation can be made portable. In addition, the testing apparatus is not sensitive to the surface state of the welds (blisters, air holes, etc).

BRIEF DESCRIPTION OF THE DRAWINGS

The invention is described in greater detail hereinafter relative to non-limitative embodiments and the attached drawings, wherein show:

FIG. 2 diagrammatically the two measuring heads according to a first embodiment of the invention.

FIG. 3 the different stages of the weld testing method according to the invention.

FIG. 4 diagrammatically a plan view of the apparatus according to a second embodiment of the invention.

FIG. 5 diagrammatically a side view of the apparatus of FIG. 4.

DETAILED DESCRIPTION OF THE PREFERRED EMBODIMENTS

In order to facilitate the description, the dimensions of the different elements described have not been respected. In addition, the welds to be inspected have been diagrammatically shown in the form of a disk or circumferences.

Figure 1:
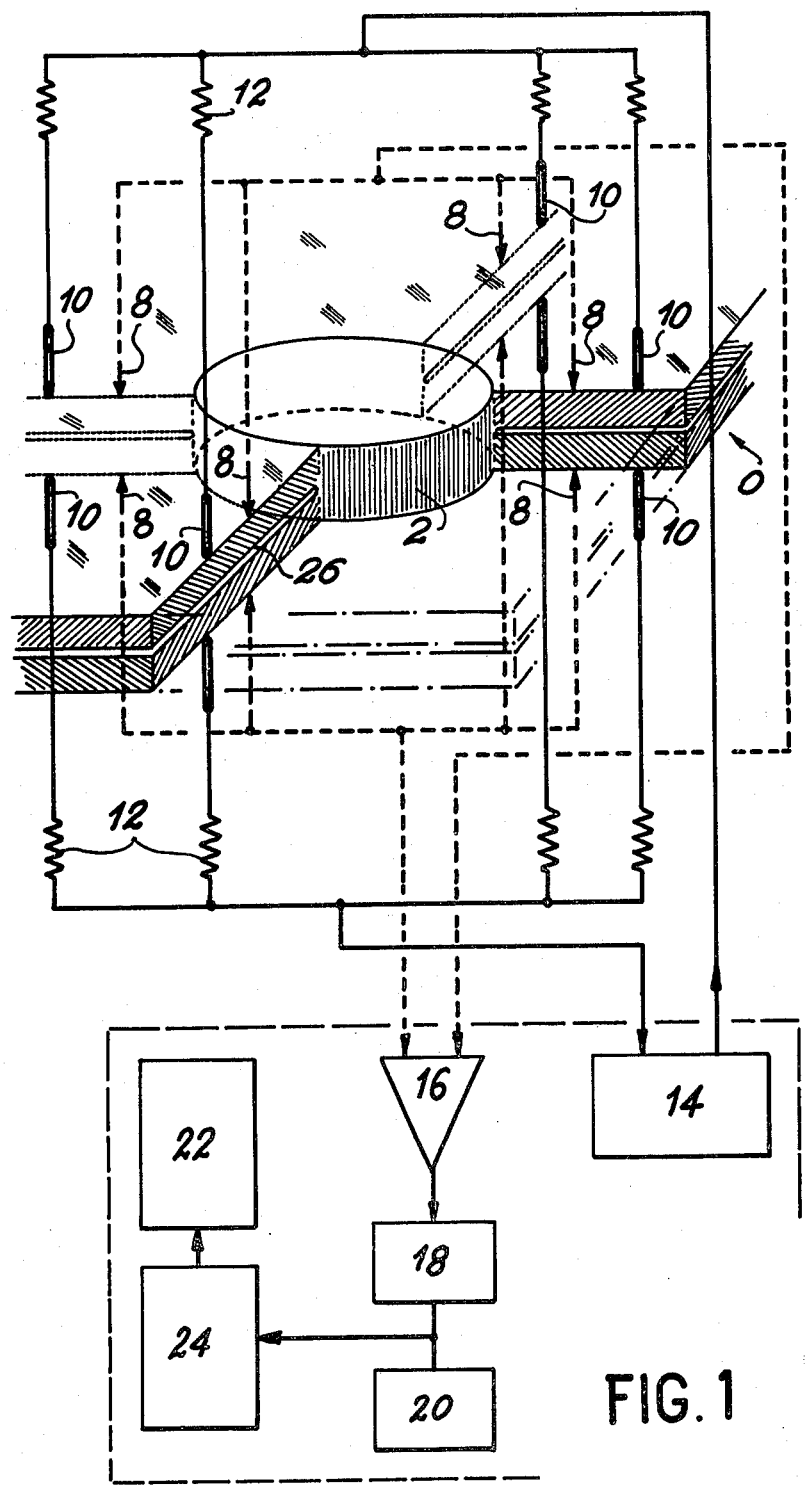
FIG. 1 a general diagram of the apparatus for the non-destructive testing of spot welds.

The weld 2 diagrammatically shown in FIG. 1 on the flat welded member 0 is placed between two identical measuring heads 4, 6, shown in FIGS. 2 and 3. Measuring head 4 represents the upper head and measuring head 6 the lower head. The measuring heads 4 and 6 in each case comprise four measuring electrodes 8 (i.e. two pairs) and four supply electrodes 10 (i.e. two pairs). The diametrically opposite measuring electrodes 8 are advantageously spaced by 11 mm and the associated supply electrodes 10 are spaced by at the most 2 mm from said measuring electrodes 8. The supply electrodes 10 of one and the same measuring head are interconnected by means of a resistor 12 of approximately 2 Ohms, so as to obtain a constant current in each circuit branch connecting each supply electrode 10 to a stabilized direct current supply 14. The latter can deliver 5 A at 8 V. The intensity fixed at 5 A (1.25 A for each supply electrode 10) is a good compromise for obtaining on the one hand an adequate final voltage and on the other for ensuring that there is no heating of the supply electrodes 10. The measuring electrodes 8 are interconnected so as to measure the resulting quantity of the potential differences measured. The voltage obtained is amplified by means of an amplifier 16 connected to an active filter 18 making it possible to eliminate background noise. The final voltage is displayed by means of a voltmeter with a digital display 20 able to detect a microvolt. When the final voltage exceeds one threshold or drops below another threshold an alarm system 22 operates. The alarm system is connected to a regulatable voltage threshold detector 24. Reference numeral 26 indicates the unwelded part of the flat member 0.

FIG. 3 shows a welded part 0 which undergoes the test according to the invention. Welded member 0 moves in the direction indicated by arrow D (the member generally being manually displaced). The weld 2 to be tested or inspected previously undergoes a mechanical test by means of a pneumatic hammer 28, provided with a die bar 30 moving in the manner indicated in the drawing. It is fixed to a column 32 and is connected to a not shown solenoid valve. After placing the weld 2 in an appropriate manner between measuring heads 4 and 6 it can be exposed to the non-destructive test. The measuring heads 4 and 6 are held in place by means of a rigid support 34. Reference numeral 36 indicates the electrical data supply cord, whilst reference numeral 38 indicates a metal plate permitting the welded member to be brought into an overhanging position.

Pneumatic hammer 28 can obviously be replaced by any other percussive tool such as a hammer, an electric hammer, a calibrated drop, a vibrating member or the like for the purpose of carrying out the mechanical test.

FIGS. 4 and 5 show a second embodiment of the apparatus. The upper measuring head 3 and the not shown lower head comprise two measuring electrodes 8 and two supply electrodes 10 arranged symmetrically with respect to weld 2. These measuring heads are used in the case of welded members 1 having a random shape. It is clear that the number n of electrode pairs used is dependent on the shape of the welded member, whose welds are to be tested (n is an integer differing from zero).

Figure 6:
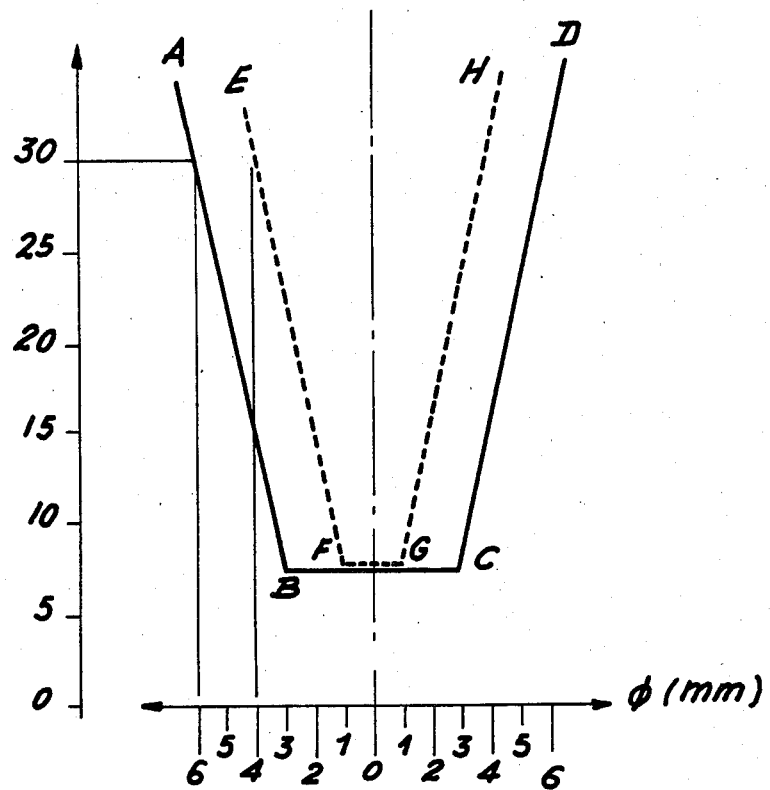
FIG. 6 the curves linking the voltage to the diameter of the weld to be inspected or tested.

FIG. 6 illustrates the rheometric method used for the non-destructive testing of spot welds according to the invention. As can be gathered from FIG. 3 the member 0 to be inspected travels between the two fixed measuring heads 4 and 6. Curves ABCD and EFGH show the voltage variation (in microvolts $\mu V$) as a function of the distance between the measuring electrodes and the centre of the WELD (given in mm). When the measuring electrodes approach the weld a linear reduction in the voltage is recorded (segment AB or EF). When the measuring electrodes overlap the weld there is an area where the voltage remains constant. This area (segment BC or FG) corresponds to the weld diameter. Finally when the measuring electrodes move away from the mould, there is a linear increase in the voltage (segment CD or GH). It should be noted that curves ABCD and EFGH are symmetrical with respect to the centre of the weld and that the optimum position of the electrodes is attained when the latter completely surround the weld to be inspected.

If the measuring electrodes are positioned 4 mm from the centre of the weld a voltage of 30 $\mu V$ is obtained for a diameter of 2 mm (curve EFGH) and a voltage of 15 $\mu V$ for a diameter of 6 mm. Thus, the voltage drops as a function of the weld diameter for a given position of the electrodes. Thus, a simple relationship exists between the voltage measured with the apparatus according to the invention and the weld diameter.

After carrying out a calibration by measuring with appropriate means different weld diameters and measuring the corresponding voltage, the weld diameter can be deduced by reading off the voltage. With the knowledge of the weld diameter it is possible to deduce efficiency. Thus, the greater the weld diameter the more effective it is.

Calibration is carried out whenever the weld type is changed. Thus, the materials forming the welded parts do not all conduct the current in the same way, so that there are variations in the voltage values. The threshold detector 22 makes it possible to regulate the inspection apparatus as a function of the voltages to be measured. The welds making it possible to carry out this calibration are removed from the welded member in such a way that they can be measured with e.g. a slide gauge (destructive testing). If the measured voltage is not within the range of the fixed thresholds an alarm 24 is set off. This makes it possible to ensure, for example, that all the electrodes are in contact with the welded member or that the weld has been destroyed during the mechanical test (infinite resistance and therefore infinite voltage).

This mechanical test makes it possible to destroy the so-called stuck or frozen welds. The mechanical test can be carried out with a pneumatic hammer regulated to approximately 7 Kg/cm$^2$. It consists of about 10 impacts, spaced by approximately 0.5 sec. Percussions take place every 90° a few mm from the edges of the weld or on the actual weld. The welded member is fixed so as to overhang a metal plate 38. It is obviously possible to use any other percussive tool for carrying out this mechanical test. This test makes it possible to differentiate three types of weld; good, mediocre and poor.

After this mechanical test, followed by calibration in the manner described hereinbefore the welds of a given member type can be inspected or tested by means of the apparatus according to the invention.

In the case of flat welded members the apparatus according to the first embodiment is used. The weld is arranged symmetrically between two measuring heads. The four electrodes (n pairs of electrodes with n equal to 2) are arranged at 90° from one another and are positioned in such a way that they surround to the optimum extent the weld to be inspected. As a result they assume a symmetrical position with respect to the weld axis. As it is not always obvious to find the axis or centre of the weld, the measuring electrodes are interconnected so as to obtain a resulting voltage.

Tests have been carried out by positioning the measuring electrodes on the weld to a greater or lesser extent. These results have shown the effectiveness of the integration system of the apparatus comprising four measuring electrodes interconnected in the manner described hereinbefore.

In the case of welds in the vicinity of the edges of the member, tests have been carried out so as to demonstrate the influence of the edges. The effects of the edges are negligible and in fact below the reproducibility of measurement for a given weld. The voltage obtained on a weld at 27 mm or 3 mm from the edges is consequently identical.

In the case of welds in the vicinity of one another an electrical coupling may exist. As a result the final voltage obtained may not be that expected. Tests on lifting cross-members performed with the apparatus according to the second embodiment (FIGS. 4 and 5) have revealed this phenomenon. In this case the centre-to-centre distance of the welds was only 10 to 15 mm (the welds were tangential or only spaced by a few mm). However, this does not constitute a limitation on the method, because the procedure is the same as for a single weld instead of separate welds.

The testing method and apparatus for spot welds make it possible to establish in a simple manner the diameter of a weld with an accuracy of ±1 mm and consequently deduce the effectiveness therefrom.

What is claimed is:

1. A method for the non-destructive testing of spot welds, wherein the welds firstly undergo a mechanical test during which the so-called "stuck" welds are destroyed and the others remain intact, which is followed by a punctiform inspection which consists of circulating, between at least one pair of electrodes in contact with the area surrounding the weld to be investigated, an electric current, then measuring a potential difference at the terminals of at least one other pair of electrodes and determining the weld diameter from said measurement by means of a calibration curve.

2. A method according to claim 1, wherein the mechanical test consists of a certain number of impacts around the welded area for a short time.

3. A method according to claim 1, wherein the mechanical test consists of a certain number of impacts on the weld for a short time.

4. A method according to claim 1, wherein the mechanical test is carried out by means of a percussion tool fixed to a column and connected to a solenoid valve ensuring the reproducibility of the impact point.

5. An apparatus for the non-destructive testing of spot welds, wherein it comprises a detection system formed by two identical measuring heads, each constituted by n pairs of measuring electrodes and n pairs of supply electrodes, each pair of said supply electrodes being associated with a pair of measuring electrodes, the two measuring heads being arranged symmetrically on the area surrounding the weld under investigation and are electrically connected to a stabilized direct current supply, to a measuring system and to a visual display device.

6. An apparatus according to claim 5, wherein each pair of measuring electrodes is aligned with the pair of supply electrodes associated therewith and is positioned symmetrically with respect to the center of the weld and the measuring electrodes of one and the same pair are spaced by at the most 11 mm and each associated supply electrode is spaced by at the most 2 mm from each measuring electrode.

7. An apparatus according to claims 5 or 6, wherein the measuring electrodes of one and the same measuring head are electrically interconnected to measure the resulting quantity of the measured potential differences.

8. An apparatus according to claim 5, wherein the supply electrodes of one and the same measuring head are interconnected by means of a resistor to obtain a constant current in each supply electrode.

* * * * *